United States Patent
Shanley et al.

(10) Patent No.: US 7,955,639 B2
(45) Date of Patent: Jun. 7, 2011

(54) SYSTEM AND METHOD FOR LOADING A BENEFICIAL AGENT INTO A MEDICAL DEVICE

(75) Inventors: John F. Shanley, Redwood City, CA (US); Stephen Hunter Diaz, Palo Alto, CA (US); Theodore L. Parker, Danville, CA (US)

(73) Assignee: Innovational Holdings, LLC., New Brunswick, NJ (US)

( * ) Notice: Subject to any disclaimer, the term of this patent is extended or adjusted under 35 U.S.C. 154(b) by 1226 days.

(21) Appl. No.: 11/392,099

(22) Filed: Mar. 28, 2006

(65) Prior Publication Data
US 2006/0222679 A1    Oct. 5, 2006

Related U.S. Application Data

(60) Provisional application No. 60/667,735, filed on Mar. 31, 2005.

(51) Int. Cl.
*B05D 3/00* (2006.01)
(52) U.S. Cl. ....... 427/2.24; 606/198; 623/1.16; 427/2.1; 427/2.14; 427/2.21; 427/2.25
(58) Field of Classification Search ................ 606/198; 623/1.16; 427/2.24
See application file for complete search history.

(56) References Cited

U.S. PATENT DOCUMENTS

| | | | |
|---|---|---|---|
| 4,733,665 A | 3/1988 | Palmaz | |
| 4,739,762 A | 4/1988 | Palmaz | |
| 4,776,337 A | 10/1988 | Palmaz | |
| 4,969,458 A | 11/1990 | Wiktor | |
| 5,716,981 A | 2/1998 | Hunter et al. | |
| 6,241,762 B1 | 6/2001 | Shanley | |
| 6,656,162 B2 | 12/2003 | Santini, Jr. et al. | |
| 6,702,849 B1 * | 3/2004 | Dutta et al. | 623/1.42 |
| 2002/0038146 A1 | 3/2002 | Harry | |
| 2002/0038767 A1 * | 4/2002 | Trozera | 205/667 |
| 2002/0082680 A1 * | 6/2002 | Shanley et al. | 623/1.16 |
| 2004/0073294 A1 | 4/2004 | Diaz et al. | |
| 2004/0202773 A1 | 10/2004 | Verlee et al. | |
| 2004/0243170 A1 * | 12/2004 | Suresh et al. | 606/198 |

FOREIGN PATENT DOCUMENTS
EP    1449546 A1    8/2004

OTHER PUBLICATIONS

European Search Report dated Aug. 5, 2010, in related Application No. 06740016.8.
International Search Report dated Sep. 18, 2006, corresponding to PCT Application No. PCT/US2006/11576.

* cited by examiner

*Primary Examiner* — Michael Barr
*Assistant Examiner* — Andrew Bowman

(57) ABSTRACT

A system for delivery of a beneficial agent in the form of a viscous liquid or paste allows holes in a medical device to be loaded in a single step process. The loading of a beneficial agent in a paste form also provides the ability to deliver large and potentially sensitive molecules including proteins, enzymes, antibodies, antisense, ribozymes, gene/vector constructs, and cells including endothelial cells.

3 Claims, 2 Drawing Sheets

SYSTEM AND METHOD FOR LOADING A BENEFICIAL AGENT INTO A MEDICAL DEVICE

CROSS REFERENCE TO RELATED APPLICATIONS

This application claims priority to U.S. Provisional Patent Application Ser. No. 60/667,735, filed Mar. 31, 2005 the entire contents of which are incorporated herein by reference.

FIELD OF THE INVENTION

The invention relates to a method and apparatus for loading a beneficial agent, such as a drug into a medical device, such as a stent.

DESCRIPTION OF THE RELATED ART

Implantable medical devices are often used for delivery of a beneficial agent, such as a drug, to an organ or tissue in the body at a controlled delivery rate over an extended period of time. These devices may deliver agents to a wide variety of bodily systems to provide a wide variety of treatments.

One of the many implantable medical devices which have been used for local delivery of beneficial agents is the coronary stent. Coronary stents are typically introduced percutaneously, and transported transluminally until positioned at a desired location. These devices are then expanded either mechanically, such as by the expansion of a mandrel or balloon positioned inside the device, or expand themselves by releasing stored energy upon actuation within the body. Once expanded within the lumen, these devices, called stents, become encapsulated within the body tissue and remain a permanent implant.

Known stent designs include monofilament wire coil stents (U.S. Pat. No. 4,969,458); welded metal cages (U.S. Pat. Nos. 4,733,665 and 4,776,337); and, most prominently, thin-walled metal cylinders with axial slots formed around the circumference (U.S. Pat. Nos. 4,733,665; 4,739,762; and 4,776,337). Known construction materials for use in stents include polymers, organic fabrics and biocompatible metals, such as stainless steel, gold, silver, tantalum, titanium, and shape memory alloys, such as Nitinol, and biodegradable materials including biodegradable polymers and biodegradable metal alloys.

Of the many problems that may be addressed through stent-based local delivery of beneficial agents, one of the most important is restenosis. Restenosis is a major complication that can arise following vascular interventions such as angioplasty and the implantation of stents. Simply defined, restenosis is a wound healing process that reduces the vessel lumen diameter by extracellular matrix deposition, neointimal hyperplasia, and vascular smooth muscle cell proliferation, and which may ultimately result in renarrowing or even reocclusion of the lumen. Despite the introduction of improved surgical techniques, devices, and pharmaceutical agents, the overall restenosis rate for bare metal stents is still reported in the range of 10% to 25% within six to twelve months after an angioplasty procedure. To treat this condition, additional revascularization procedures are frequently required, thereby increasing trauma and risk to the patient.

One of the techniques recently introduced to address the problem of restenosis is the use of surface coatings of various drugs on stents. Surface coatings, however, can provide little actual control over the release kinetics of beneficial agents. These coatings are necessarily very thin, typically 5 to 8 microns deep. The surface area of the stent, by comparison is very large, so that the entire volume of the beneficial agent has a very short diffusion path to discharge into the surrounding tissue.

Increasing the thickness of the surface coating has the beneficial effects of improving drug release kinetics including the ability to control drug release and to allow increased drug loading. However, the increased coating thickness results in increased overall thickness of the stent wall and increased risk of cracking, flaking, or separating from the stent.

In addition, it is not currently possible to deliver many drugs with a surface coating due to sensitivity of the drugs to water, other compounds, or conditions in the body which degrade the drugs. Lack of drug capacity and lack of control over delivery also limit the usefulness of surface coatings for many drugs.

U.S. Patent Publication 2004/0073294 describes systems and methods for loading a beneficial agent into holes in a medical device, such as a stent. This process uses a computer guided micro dispenser to load droplets of liquid solution into the holes of the stent. The stents are mounted on a rubber coated mandrel blocking the bottoms of the holes. A machine, using machine vision, maps the exact locations of each of the target holes and then moves each hole under the dispenser that then loads liquid into the holes. The filled stent is dried in an oven, and then a next deposit is applied. Subsequent deposits of polymer and polymer/drug are applied to achieve the desired release properties.

This process has some advantages. It is a non-contact process, so there is little drag of material from hole to hole and no back contamination. It is very fast, filling at least 10 holes per second. The dispenser can be turned on and off very quickly, so complex patterns of filling can be supported. It has proven results of accuracy and consistency.

The liquid droplet method also has some limitations. The piezoelectric dispenser generally requires solutions with low viscosities. Therefore, the solids content should remain low, often less than 5%. The low solids content can result in the need for many deposits to build up a sufficient amount of beneficial agent. In addition, the solid should be very soluble in the solvent. This may require the use of solvents that have undesirable properties. Finally, the oven drying step is too hot for some drugs or sensitive proteins.

Accordingly, it would be desirable to provide a system and method for loading a beneficial agent into an expandable medical device, such as a stent, which can deliver compositions with higher solids content and/or can operate with limited drying time or low drying temperature.

It would also be desirable to provide a system and method for loading beneficial agents such as agents with little or no shelf life into a medical device just prior to use of the medical device.

SUMMARY OF THE INVENTION

The present invention relates to a system and method for loading a beneficial agent in a medical device wherein the beneficial agent is in the form of paste.

In accordance with one aspect of the invention, a method for loading a medical device with a beneficial agent comprises the steps of providing a medical device with an exterior surface and a plurality of holes intersecting the exterior surface, delivering a beneficial agent into the plurality of holes in a paste form and forming a drug delivery device with substantially no beneficial agent on the exterior surface of the medical device.

In accordance with another aspect of the invention, a system for loading a medical device with a beneficial agent comprises a medical device with an exterior surface and a plurality of holes intersecting the exterior surface, a source of beneficial agent in a paste form and a fixture configured to contain the medical device and deliver the beneficial agent into the plurality of holes with substantially no beneficial agent on the exterior surface of the medical device.

BRIEF DESCRIPTION OF THE DRAWINGS

The invention will now be described in greater detail with reference to the preferred embodiments illustrated in the accompanying drawings, in which like elements bear like reference numerals.

DETAILED DESCRIPTION OF THE INVENTION

Figure 1:
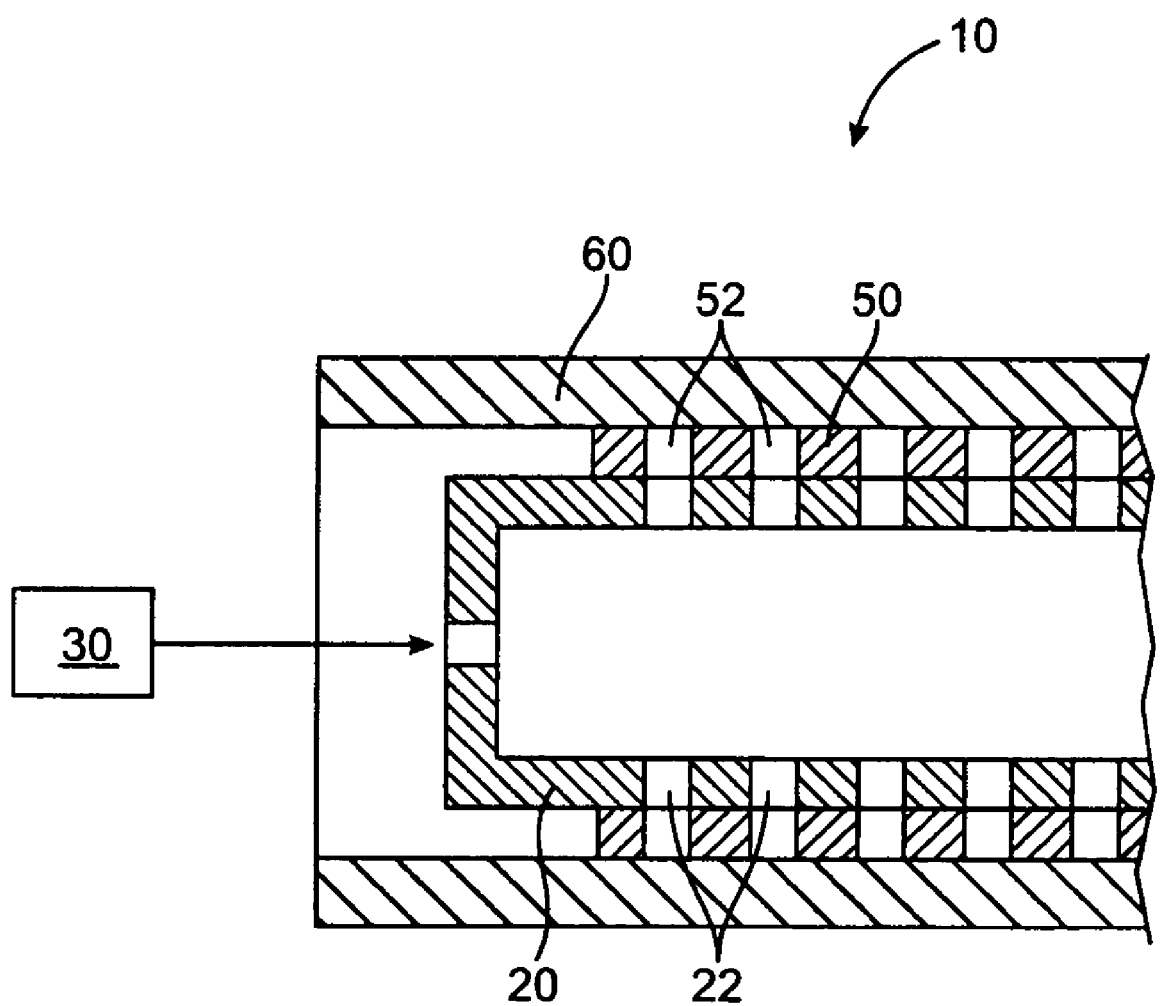
FIG. 1 is a side cross sectional view of a portion of a medical device and a system for loading a beneficial agent into the medical device.

The present invention relates to a method and apparatus for loading a beneficial agent into a medical device. More particularly, the invention relates to a method and apparatus for loading a beneficial agent in a stent. The beneficial agent which is loaded into the medical device is in a paste form.

First, the following terms, as used herein, shall have the following meanings:

The term "beneficial agent" as used herein is intended to have its broadest possible interpretation and is used to include any therapeutic agent or drug, as well as inactive agents such as barrier layers, carrier layers, therapeutic layers or protective layers.

The terms "drug" and "therapeutic agent" are used interchangeably to refer to any therapeutically active substance that is delivered to a living being to produce a desired, usually beneficial, effect. The present invention is particularly well suited for the delivery of antineoplastic, angiogenic factors, immuno-suppressants, anti-inflammatories and antiproliferatives (anti-restenosis agents) such as paclitaxel and Rapamycin for example, and antithrombins such as heparin, for example. The present invention is also well suited for delivery of larger and potentially sensitive molecules including proteins and stem cells.

The term "matrix" or "biocompatible matrix" are used interchangeably to refer to a medium or material that, upon implantation in a subject, does not elicit a detrimental response sufficient to result in the rejection of the matrix. The matrix typically does not provide any therapeutic responses itself, though the matrix may contain or surround a therapeutic agent, a therapeutic agent, an activating agent or a deactivating agent, as defined herein. A matrix is also a medium that may simply provide support, structural integrity or structural barriers. The matrix may be polymeric, non-polymeric, hydrophobic, hydrophilic, lipophilic, amphiphilic, and the like.

The term "bioresorbable" refers to a matrix, as defined herein, that can be broken down by either chemical or physical process, upon interaction with a physiological environment. The bioresorbable matrix is broken into components that are metabolizable or excretable, over a period of time from minutes to years, preferably less than one year, while maintaining any requisite structural integrity in that same time period.

The term "polymer" refers to molecules formed from the chemical union of two or more repeating units, called monomers. Accordingly, included within the term "polymer" may be, for example, dimers, trimers and oligomers. The polymer may be synthetic, naturally-occurring or semisynthetic. In preferred form, the term "polymer" refers to molecules which typically have a $M_w$ greater than about 3000 and preferably greater than about 10,000 and a $M_w$ that is less than about 10 million, preferably less than about a million and more preferably less than about 200,000.

The term "holes" refers to holes of any shape and includes both through-holes and recesses.

Implantable Medical Devices with Holes

U.S. Pat. No. 6,241,762 illustrates a medical device in the form of a stent designed with large, non-deforming struts, which can contain holes without compromising the mechanical properties of the struts, or the device as a whole. The non-deforming struts can be achieved by the use of ductile hinges which are described in detail in U.S. Pat. No. 6,241,762, which is incorporated hereby by reference in its entirety. The holes serve as large, protected reservoirs for delivering various beneficial agents to the device implantation site. The stent described above or any other known stent can be provided with holes for delivery of beneficial agents according to the present invention.

The holes can be circular, oval, rectangular, polygonal, D-shaped, or other shaped and can extend through the thickness of the medical device. The volume of beneficial agent that can be delivered using holes is about 3 to 10 times greater than the volume of a 5 micron coating covering a stent with the same stent/vessel wall coverage ratio. This much larger beneficial agent capacity provides several advantages. The larger capacity can be used to deliver multi-drug combinations, each with independent release profiles, for improved efficacy. Also, larger capacity can be used to provide larger quantities of less aggressive drugs to achieve clinical efficacy without the undesirable side-effects of more potent drugs.

According to one example, the total depth of the holes is about 100 to about 140 microns (about 0.0039 to about 0.0055 inches), typically 125 microns (0.0049 inches) for stainless steel. For stronger alloys, such as commercially available cobalt chromium alloys, the stent may be somewhat thinner. For example, the total depth of the holes is about 60 to about 100 microns (about 0.0026 to about 0.0039 inches) for cobalt chromium alloys. According to one preferred embodiment of the present invention, each of the holes have an area of at least $5 \times 10^{-6}$ square inches, and preferably at least $10 \times 10^{-6}$ square inches. A square hole having a width of about 0.005 inches will have an hole area of about $25 \times 10^{-6}$ square inches.

Uses for Implantable Medical Devices

Although the present invention has been described with reference to a medical device in the form of a stent, the medical devices of the present invention can also be medical devices of other shapes useful for site-specific and time-release delivery of drugs to the body including the heart and other organs and tissues. The drugs may be delivered to the vasculature including the coronary and peripheral vessels for a variety of therapies, and to other lumens in the body. The drugs may increase lumen diameter, create occlusions, or deliver the drug for other reasons. The medical devices can take a variety of shapes including cylinders, spheres, coils, filament, mesh, and other shapes.

Medical devices and stents, as described herein, are useful for the prevention of amelioration of restenosis, particularly after percutaneous transluminal coronary angioplasty and intraluminal stent placement. In addition to the timed or sustained release of anti-restenosis agents, other agents such as anti-inflammatory agents and immunosuppressant agents may be incorporated into the microstructures incorporated in the plurality of holes within the device. This allows for site-specific treatment or prevention of any complications routinely associated with stent placements that are known to occur at very specific times after the placement occurs.

A size and number of the holes will depend on the particular medical device, beneficial agent, and treatment desired. For example, the width of the holes can vary from about 0.001 inches to about 0.1 inches, preferably about 0.001 inches to about 0.05 inches.

Systems and Methods for Loading a Beneficial Agent into a Medical Device

FIG. 1 illustrates a system 10 for delivery of a beneficial agent in the form of a viscous liquid or paste into the holes in a medical device. The device of FIG. 1 allows the holes to be loaded in a single step process. The loading of a beneficial agent in a paste form also provides the ability to deliver large and potentially sensitive molecules including proteins, enzymes, antibodies, antisense, ribozymes, gene/vector constructs, and cells including endothelial cells.

The system for filling the holes with a beneficial agent, such as a drug/polymer mixture or protein, which pumps the beneficial agent as a thick paste into the holes can include various fixtures which hold the stent and direct the paste into the holes. In one example, the paste has a viscosity of at least 300 centipoise at 70° F., preferably at least 1000 centipoise at 70° F.

In one example, the system for delivering paste into the holes according to FIG. 1 includes a fixture in the form of a tube or mandrel 20 fabricated with a plurality of fixture holes 22 that exactly match the holes in the stent. A paste source 30 is provided for delivery of the paste to the mandrel 20. The medical device or stent 50 is then placed onto the mandrel 20 and the stent holes 52 are aligned with the fixture holes 22. A close fitting outer cylinder 60 is placed around the stent and tube to press the stent firmly against the tube with the holes. The outer cylinder 60 can be a porous tube which allows air to flow through without allowing the larger molecules of the beneficial agent to flow through. Porous tubes suitable for the outer cylinder 60 include sintered materials such as Mott porous metal filters. The paste can be pumped by any known pumping system from the source 30 into the holes 52 through the fixture tube under great pressure until the holes are partially and completely full. This arrangement prevents the paste from being loaded onto the inner or outer surfaces of the stent 50 and positions all of the beneficial agent within the holes 52 in the stent.

The paste can include one or more of a drug, a matrix, a solvent, and other additives. The solvent for the paste can be one that doesn't dissolve the polymer, but simply holds particles of polymer and/or drug together. After this particle paste is in place in the holes, the entire stent can be dunked in a more aggressive solvent to fuse the particles and bind them to the walls of the holes. The beneficial agent in the holes can be cured to a hard state or remain in a paste state, as the holes act as protective reservoirs for the beneficial agent and prevent the beneficial agent from being scrapped off as occurs with a surface coating.

Alternately, the polymer and/or drug can be dissolved in the solvent to form a paste and the paste can be injected under pressure into the holes 52 in the stent 50. The solvent can subsequently be evaporated to secure the beneficial agent in the holes.

The fixture tube or mandrel 20 with the holes 22 can be fabricated with known laser technologies such as those used to cut stents, so a close match between the stent 50 and the fixture will be possible. In some cases, the stents can get a little bent or twisted in the process of polishing and inspection and thus, the stents may need to be straightened to be properly mounted onto the mandrel.

In one embodiment, the twisted stent can be straightened back to close alignment with its original shape by forcing the stent 50 onto a cylinder with "bumps" that urge the stent back into its original shape. There can be a series of "bumped" rollers that fit the stent struts closer and closer so the reshaping process can take place in stages.

In another embodiment, the mandrel 20 can be formed from a solid tube and the holes 22 can be formed by machine vision laser cutting the holes after the stent 50 is mounted on the mandrel. In order to prevent damage to the stent 50, a material for the mandrel 20 and the laser properties of the laser can be selected so that the stent is unaffected.

Figure 2:
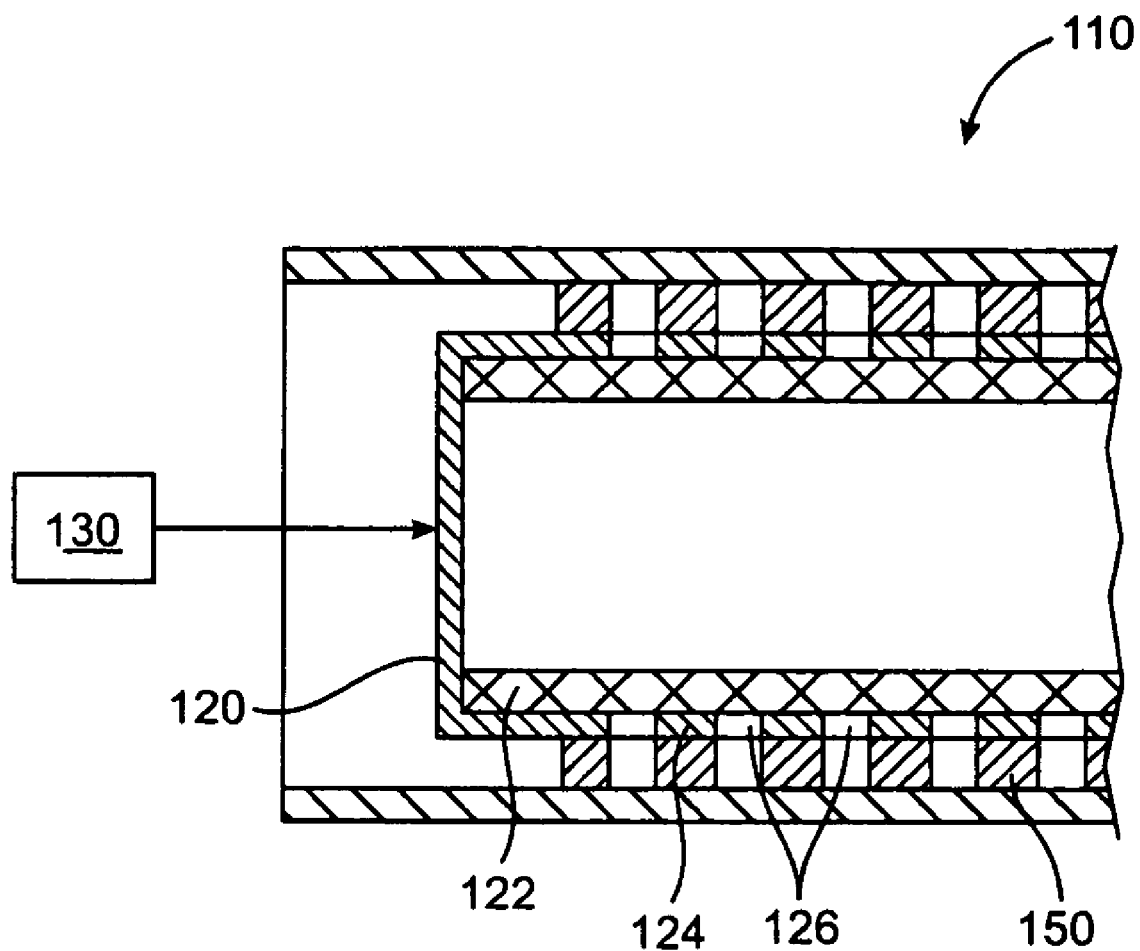
FIG. 2 is a side cross sectional view of a portion of a medical device and an alternative system for loading a beneficial agent into the medical device.

FIG. 2 illustrates another embodiment of a system for delivering a beneficial agent paste into the holes. In the system 110 of FIG. 2, the mandrel 120 can be formed in multiple parts or layers with a first layer 122 with many holes, more like a screen, so that no matter what the stent shape, each hole in the stent 150 would line up with a hole in the screen. A very thin polymer tube or other material 124 can be slipped over the screen layer 122, blocking all the holes. The stent 150 would be positioned over this tube, and then a machine vision laser would be guided over each hole 152 in the stent to be filled and the polymer 124 can be burned away at the locations of the holes in the stent to form holes 126 in the polymer layer. Then, when the paste was pumped from the source 130 into the hollow mandrel 120, it will flow through the mesh 122 and out the laser cut holes 126 in the polymer sleeve 124 and into the holes 152 in the stent 150. Alternatively, the stent can be used as a "self mask" during this laser cutting process similar to the masking technique used in silicone chip manufacture.

The paste method is especially appealing for fragile protein pastes, stem cells, or other materials having a short shelf life. Some of these materials cannot be preloaded onto stents or other delivery devices and stored for prolonged periods, such as six months. Other materials can be loaded just shortly prior to use. For example, a stent or other medical device can be loaded with a beneficial agent paste in the doctor's office, catheter lab, or operating room just prior to a procedure.

A simple loading system can be provided to allow the stent to be loaded by hospital personnel. In the operating room, the fixture would be attached to a simple pump and a custom paste could be pumped into the holes. The filled stent can then be immediately crimped on the catheter and inserted into the patient.

In a syringe type on site loading system, the stent is preloaded onto the fitting tube or mandrel with corresponding holes. This system can be delivered to the user without the beneficial agent paste and the paste can be delivered or prepared separately. The paste can be drawn into the fitting tube with a syringe plunger which is a part of or separate from the fitting or by connection to a vacuum source. The tube can be capped and the entire assembly is sterilized. Pressure can be applied by the syringe plunger or by another pressure source to deliver the paste from inside the mandrel into the stent holes. This would fill the holes without filling other places, such as between the stent struts.

The on site loading system can also incorporate a crimping mechanism for crimping the stent onto a balloon. The loading and crimping processes can be combined in one device such that the stent is loaded by a first step, the mandrel is removed, the catheter is then inserted, and the stent is crimped in onto the catheter.

In one embodiment, the paste delivered into the holes can be loaded in layers with different compositions or concentrations in the layers. Different layers can be comprised of different therapeutic agents altogether, creating the ability to release different therapeutic agents at different points in time. The layers of beneficial agent provide the ability to tailor a drug delivery profile to different applications. This allows the medical device according to the present invention to be used for delivery of different beneficial agents to a wide variety of locations in the body. Alternately, different holes can be filled with different agents by providing two or more steps of filing with different mandrels having different sets of holes corresponding to the holes in the stent.

A protective layer in the form of a cap layer can be provided at a tissue contacting surface of the stent. A base layer can also be used on the luminal surface of the stent. The cap and base layers can provide directional delivery by prevent the therapeutic agent from passing through one of the cap or base layer and can delay or retard delivery to achieve a desired release kinetic.

Other therapeutic agents for use with the present invention may, for example, take the form of small molecules, peptides, lipoproteins, polypeptides, polynucleotides encoding polypeptides, lipids, protein-drugs, protein conjugate drugs, enzymes, oligonucleotides and their derivatives, ribozymes, other genetic material, cells, antisense oligonucleotides, monoclonal antibodies, platelets, prions, viruses, bacteria, eukaryotic cells such as endothelial cells, stem cells, ACE inhibitors, monocyte/macrophages and vascular smooth muscle cells. Such agents can be used alone or in various combinations with one another. For instance, anti-inflammatories may be used in combination with antiproliferatives to mitigate the reaction of tissue to the antiproliferative. The therapeutic agent may also be a pro-drug, which metabolizes into the desired drug when administered to a host. In addition, therapeutic agents may be pre-formulated as microcapsules, microspheres, microbubbles, liposomes, niosomes, emulsions, dispersions or the like before they are incorporated into the matrix. Therapeutic agents may also be radioactive isotopes or agents activated by some other form of energy such as light or ultrasonic energy, or by other circulating molecules that can be systemically administered.

Exemplary classes of therapeutic agents include antiproliferatives, antithrombins (i.e., thrombolytics), immunosuppressants, antilipid agents, anti-inflammatory agents, antineoplastics including antimetabolites, antiplatelets, angiogenic agents, anti-angiogenic agents, vitamins, antimitotics, metalloproteinase inhibitors, NO donors, nitric oxide release stimulators, anti-sclerosing agents, vasoactive agents, endothelial growth factors, beta blockers, AZ blockers, hormones, statins, insulin growth factors, antioxidants, membrane stabilizing agents, calcium antagonists (i.e., calcium channel antagonists), retinoids, anti-macrophage substances, anti-lymphocytes, cyclooxygenase inhibitors, immunomodulatory agents, angiotensin converting enzyme (ACE) inhibitors, anti-leukocytes, high-density lipoproteins (HDL) and derivatives, cell sensitizers to insulin, prostaglandins and derivatives, anti-TNF compounds, hypertension drugs, protein kinases, antisense oligonucleotides, cardio protectants, petidose inhibitors (increase blycolitic metabolism), endothelin receptor agonists, interleukin-6 antagonists, anti-restenotics, vasodilators, and other miscellaneous compounds.

Antiproliferatives include, without limitation, paclitaxel, actinomycin D, rapamycin, everolimus, ZoMaxx, tacrolimus, cyclosporin, and pimecrolimus.

Antithrombins include, without limitation, heparin, aspirin, sulfinpyrazone, ticlopidine, ABCIXIMAB, eptifibatide, tirofiban HCL, coumarines, plasminogen, $\alpha_2$-antiplasmin, streptokinase, urokinase, bivalirudin, tissue plasminogen activator (t-PA), hirudins, hirulogs, argatroban, hydroxychloroquin, BL-3459, pyridinolcarbamate, Angiomax, and dipyridamole.

Immunosuppressants include, without limitation, cyclosporine, rapamycin and tacrolimus (FK-506), ZoMaxx, everolimus, etoposide, and mitoxantrone.

Antilipid agents include, without limitation, HMG CoA reductase inhibitors, nicotinic acid, probucol, and fibric acid derivatives (e.g., clofibrate, gemfibrozil, gemfibrozil, fenofibrate, ciprofibrate, and bezafibrate).

Anti-inflammatory agents include, without limitation, pimecrolimus, salicylic acid derivatives (e.g., aspirin, insulin, sodium salicylate, choline magnesium trisalicylate, salsalate, dflunisal, salicylsalicylic acid, sulfasalazine, and olsalazine), para-amino phenol derivatives (e.g., acetaminophen), indole and indene acetic acids (e.g., indomethacin, sulindac, and etodolac), heteroaryl acetic acids (e.g., tolmetin, diclofenac, and ketorolac), arylpropionic acids (e.g., ibuprofen, naproxen, flurbiprofen, ketoprofen, fenoprofen, and oxaprozin), anthranilic acids (e.g., mefenamic acid and meclofenamic acid), enolic acids (e.g., piroxicam, tenoxicam, phenylbutazone and oxyphenthatrazone), alkanones (e.g., nabumetone), glucocorticoids (e.g., dexamethaxone, prednisolone, and triamcinolone), pirfenidone, and tranilast.

Antineoplastics include, without limitation, nitrogen mustards (e.g., mechlorethamine, cyclophosphamide, ifosfamide, melphalan, and chlorambucil), methylnitrosoureas (e.g., streptozocin), 2-chloroethylnitrosoureas (e.g., carmustine, lomustine, semustine, and chlorozotocin), alkanesulfonic acids (e.g., busulfan), ethylenimines and methylmelamines (e.g., triethylenemelamine, thiotepa and altretamine), triazines (e.g., dacarbazine), folic acid analogs (e.g., methotrexate), pyrimidine analogs (5-fluorouracil, 5-fluorodeoxyuridine, 5-fluorodeoxyuridine monophosphate, cytosine arabinoside, 5-azacytidine, and 2',2'-difluorodeoxycytidine), purine analogs (e.g., mercaptopurine, thioguanine, azathioprine, adenosine, pentostatin, cladribine, and erythrohydroxynonyladenine), antimitotic drugs (e.g., vinblastine, vincristine, vindesine, vinorelbine, paclitaxel, docetaxel, epipodophyllotoxins, dactinomycin, daunorubicin, doxorubicin, idarubicin, epirubicin, mitoxantrone, bleomycins, plicamycin and mitomycin), phenoxodiol, etoposide, and platinum coordination complexes (e.g., cisplatin and carboplatin).

Antiplatelets include, without limitation, insulin, dipyridamole, tirofiban, eptifibatide, abciximab, and ticlopidine.

Angiogenic agents include, without limitation, phospholipids, ceramides, cerebrosides, neutral lipids, triglycerides, diglycerides, monoglycerides lecithin, sphingosides, angiotensin fragments, nicotine, pyruvate thiolesters, glycerolpyruvate esters, dihydoxyacetone-pyruvate esters and monobutyrin.

Anti-angiogenic agents include, without limitation, endostatin, angiostatin, fumagillin and ovalicin.

Vitamins include, without limitation, water-soluble vitamins (e.g., thiamin, nicotinic acid, pyridoxine, and ascorbic acid) and fat-soluble vitamins (e.g., retinal, retinoic acid, retinaldehyde, phytonadione, menaqinone, menadione, and alpha tocopherol).

Antimitotics include, without limitation, vinblastine, vincristine, vindesine, vinorelbine, paclitaxel, docetaxel, epipodophyllotoxins, dactinomycin, daunorubicin, doxorubicin, idarubicin, epirubicin, mitoxantrone, bleomycins, plicamycin and mitomycin.

Metalloproteinase inhibitors include, without limitation, TIMP-1, TIMP-2, TIMP-3, and SmaPI.

NO donors include, without limitation, L-arginine, amyl nitrite, glyceryl trinitrate, sodium nitroprusside, molsidomine, diazeniumdiolates, S-nitrosothiols, and mesoionic oxatriazole derivatives.

NO release stimulators include, without limitation, adenosine.

Anti-sclerosing agents include, without limitation, collagenases and halofuginone.

Vasoactive agents include, without limitation, nitric oxide, adenosine, nitroglycerine, sodium nitroprusside, hydralazine, phentolamine, methoxamine, metaraminol, ephedrine, trapadil, dipyridamole, vasoactive intestinal polypeptides (VIP), arginine, and vasopressin.

Endothelial growth factors include, without limitation, VEGF (Vascular Endothelial Growth Factor) including VEGF-121 and VEG-165, FGF (Fibroblast Growth Factor) including FGF-1 and FGF-2, HGF (Hepatocyte Growth Factor), and Ang1 (Angiopoietin 1).

Beta blockers include, without limitation, propranolol, nadolol, timolol, pindolol, labetalol, metoprolol, atenolol, esmolol, and acebutolol.

Hormones include, without limitation, progestin, insulin, the estrogens and estradiols (e.g., estradiol, estradiol valerate, estradiol cypionate, ethinyl estradiol, mestranol, quinestrol, estrond, estrone sulfate, and equilin).

Statins include, without limitation, mevastatin, lovastatin, simvastatin, pravastatin, atorvastatin, and fluvastatin.

Insulin growth factors include, without limitation, IGF-1 and IGF-2.

Antioxidants include, without limitation, vitamin A, carotenoids and vitamin E.

Membrane stabilizing agents include, without limitation, certain beta blockers such as propranolol, acebutolol, labetalol, oxprenolol, pindolol and alprenolol.

Calcium antagonists include, without limitation, amlodipine, bepridil, diltiazem, felodipine, isradipine, nicardipine, nifedipine, nimodipine and verapamil.

Retinoids include, without limitation, all-trans-retinol, all-trans-14-hydroxyretroretinol, all-trans-retinaldehyde, all-trans-retinoic acid, all-trans-3,4-didehydroretinoic acid, 9-cis-retinoic acid, 11-cis-retinal, 13-cis-retinal, and 13-cis-retinoic acid.

Anti-macrophage substances include, without limitation, NO donors.

Anti-leukocytes include, without limitation, 2-CdA, IL-1 inhibitors, anti-CD116/CD18 monoclonal antibodies, monoclonal antibodies to VCAM, monoclonal antibodies to ICAM, and zinc protoporphyrin.

Cyclooxygenase inhibitors include, without limitation, Cox-1 inhibitors and Cox-2 inhibitors (e.g., CELEBREX® and VIOXX®).

Immunomodulatory agents include, without limitation, immunosuppressants (see above) and immunostimulants (e.g., levamisole, isoprinosine, Interferon alpha, and Interleukin-2).

ACE inhibitors include, without limitation, benazepril, captopril, enalapril, fosinopril sodium, lisinopril, quinapril, ramipril, spirapril, and 2B3 ACE inhibitors.

Cell sensitizers to insulin include, without limitation, glitazones, P PAR agonists and metformin.

Antisense oligonucleotides include, without limitation, resten-NG.

Cardio protectants include, without limitation, VIP, pituitary adenylate cyclase-activating peptide (PACAP), apoA-I milano, amlodipine, nicorandil, cilostaxone, and thienopyridine.

Petidose inhibitors include, without limitation, omnipatrilat.

Anti-restenotics include, without limitation, include vincristine, vinblastine, actinomycin, epothilone, paclitaxel, paclitaxel derivatives (e.g., docetaxel), rapamycin, rapamycin derivatives, everolimus, tacrolimus, ZoMaxx, and pimecrolimus.

PPAR gamma agonists include, without limitation, farglitizar, rosiglitazone, muraglitazar, pioglitazone, troglitazone, and balaglitazone.

Miscellaneous compounds include, without limitation, Adiponectin.

Agents may also be delivered using a gene therapy-based approach in combination with an expandable medical device. Gene therapy refers to the delivery of exogenous genes to a cell or tissue, thereby causing target cells to express the exogenous gene product. Genes are typically delivered by either mechanical or vector-mediated methods.

Some of the agents described herein may be combined with additives which preserve their activity. For example additives including surfactants, antacids, antioxidants, and detergents may be used to minimize denaturation and aggregation of a protein drug. Anionic, cationic, or nonionic detergents may be used. Examples of nonionic additives include but are not limited to sugars including sorbitol, sucrose, trehalose; dextrans including dextran, carboxy methyl (CM) dextran, diethylamino ethyl (DEAE) dextran; sugar derivatives including D-glucosaminic acid, and D-glucose diethyl mercaptal; synthetic polyethers including polyethylene glycol (PEF and PEO) and polyvinyl pyrrolidone (PVP); carboxylic acids including D-lactic acid, glycolic acid, and propionic acid; detergents with affinity for hydrophobic interfaces including n-dodecy-☐-D-maltoside, n-octyl-☐-D-glucoside, PEO-fatty acid esters (e.g. stearate (myrj 59) or oleate), PEO-sorbitan-fatty acid esters (e.g. Tween 80, PEO-20 sorbitan monooleate), sorbitan-fatty acid esters (e.g. SPAN 60, sorbitan monostearate), PEO-glyceryl-fatty acid esters; glyceryl fatty acid esters (e.g. glyceryl monostearate), PEO-hydrocarbon-ethers (e.g. PEO-10 oleyl ether; triton X-100; and Lubrol. Examples of ionic detergents include but are not limited to fatty acid salts including calcium stearate, magnesium stearate, and zinc stearate; phospholipids including lecithin and phosphatidyl choline; CM-PEG; cholic acid; sodium dodecyl sulfate (SDS); docusate (AOT); and taumocholic acid.

While the invention has been described in detail with reference to the preferred embodiments thereof, it will be apparent to one skilled in the art that various changes and modifications can be made and equivalents employed, without departing from the present invention.

What is claimed is:

1. A method for loading a medical device with a beneficial agent, the method comprising:
   providing a medical device with an exterior surface and a plurality of holes intersecting the exterior surface;
   delivering a beneficial agent into the plurality of holes in a paste form through a fixture having a plurality of fixture holes which are aligned with the plurality of holes of the medical device; and
   forming a drug delivery device with substantially no beneficial agent on the exterior surface of the medical device, wherein the fixture is a tube having the plurality of fixture holes formed in the surface of the tube and the medical device mounted on an exterior surface of the tube.

2. A method for loading a medical device with a beneficial agent, the method comprising:
providing a medical device with an exterior surface, an interior surface, and a plurality of holes intersecting the exterior surface and the interior surface;
mounting the medical device on a tube;
cutting a plurality of holes in the tube to match the plurality of holes in the medical device;
delivering a beneficial agent into the plurality of holes in a paste form; and
forming a drug delivery device with substantially no beneficial agent on the exterior surface of the medical device.

3. A method for loading a medical device with a beneficial agent, the method comprising:
providing a medical device with an exterior surface, an interior surface, and a plurality of holes intersecting the exterior surface and the interior surface;
mounting the medical device on a mandrel comprising a tubular shaped mesh layer and a polymer sleeve in contact with an outer diameter of the tubular shaped mesh layer;
cutting a plurality of holes in the polymer sleeve;
delivering a beneficial agent into the plurality of holes in a paste form; and
forming a drug delivery device with substantially no beneficial agent on the exterior surface of the medical device,
wherein cutting a plurality of holes comprises burning away the polymer sleeve at the locations of the plurality of holes in the medical device.

* * * * *